(12) United States Patent
Zhang et al.

(10) Patent No.: US 10,948,407 B2
(45) Date of Patent: Mar. 16, 2021

(54) METHOD FOR DETECTING MULTIVARIATE ADULTERATION OF EDIBLE OIL BASED ON NEAR-INFRARED SPECTROSCOPY

(71) Applicant: OIL CROPS RESEARCH INSTITUTE, CHINESE ACADAMY OF AGRICULTURAL SCIENCES, Hubei (CN)

(72) Inventors: Liangxiao Zhang, Hubei (CN); Peiwu Li, Hubei (CN); Zhe Yuan, Hubei (CN); Du Wang, Hubei (CN); Xuefang Wang, Hubei (CN); Wen Zhang, Hubei (CN); Qi Zhang, Hubei (CN)

(73) Assignee: OIL CROPS RESEARCH INSTITUTE, CHINESE ACADAMY OF AGRICULTURAL SCIENCES, Hubei (CN)

( * ) Notice: Subject to any disclaimer, the term of this patent is extended or adjusted under 35 U.S.C. 154(b) by 282 days.

(21) Appl. No.: 16/197,689

(22) Filed: Nov. 21, 2018

(65) Prior Publication Data

US 2019/0162658 A1 May 30, 2019

(30) Foreign Application Priority Data

Nov. 24, 2017 (CN) .......................... 201711194143.0

(51) Int. Cl.
*G01N 21/359* (2014.01)
*G01N 33/03* (2006.01)
*G01N 21/3577* (2014.01)

(52) U.S. Cl.
CPC ....... *G01N 21/359* (2013.01); *G01N 21/3577* (2013.01); *G01N 33/03* (2013.01); *G01N 2201/129* (2013.01)

(58) Field of Classification Search
CPC ... G01N 21/359; G01N 21/3577; G01N 33/03
(Continued)

(56) References Cited

U.S. PATENT DOCUMENTS

2013/0017298 A1* 1/2013 Wang ..................... G01N 21/65
426/231
2017/0299506 A1* 10/2017 Azizian .............. G01N 21/3577
(Continued)

FOREIGN PATENT DOCUMENTS

WO WO-2016141451 A1 * 9/2016 ............. G01N 33/03

*Primary Examiner* — Ricky Ngon
(74) *Attorney, Agent, or Firm* — Tim Tingkang Xia, Esq.; Locke Lord LLP (57) ABSTRACT

A method for multivariate adulteration detection on an edible oil includes (1) construction of a model: S1, acquiring near-infrared spectra of edible oils; S2, establishing a near-infrared spectral database of the edible oils; S3, establishing a multivariate adulteration detection model for a type of edible oil; and (2) application of the model: acquiring spectra of a sample to be tested according to the near-infrared spectral signal acquisition method in step S1, pre-processing the obtained near-infrared spectra by using the method in step S2 to obtain near-infrared spectral data of the sample, and determining the authenticity of the sample to be tested by using the multivariate adulteration detection model for the edible oil established in step S3. The method is simple and rapid in operation, can effectively and rapidly screen the authenticity of an edible vegetable oil, and has strong practicability.

13 Claims, 3 Drawing Sheets

(58) Field of Classification Search
USPC ............................................................ 702/28
See application file for complete search history.

(56) References Cited

U.S. PATENT DOCUMENTS

2018/0085003 A1\* 3/2018 Goldring ................ G01N 21/27
2018/0276597 A1\* 9/2018 Fuller ................... H04L 9/3247
2018/0364210 A1\* 12/2018 Yao ..................... H01J 49/0009

\* cited by examiner

METHOD FOR DETECTING MULTIVARIATE ADULTERATION OF EDIBLE OIL BASED ON NEAR-INFRARED SPECTROSCOPY

CROSS-REFERENCE TO RELATED APPLICATION

This non-provisional application claims priority to and benefit of Chinese Patent Application No. 201711194143.0, filed Nov. 24, 2017 in the State Intellectual Property Office of P.R. China, which is hereby incorporated by reference in its entirety.

FIELD OF THE INVENTION

The present invention relates generally to the field of food quality and safety, and more particularly to a method for detecting multivariate adulteration of edible oil based on near-infrared spectroscopy.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

Edible oils are important food, providing energy, essential fatty acids, and rich nutrient and functional ingredients such as phytosterols, vitamin E, phenols and lignans for human beings. Linseed oil, olive oil and peanut oil are favored by consumers because of their high nutritional and medicinal values as a kind of high-grade edible vegetable oil, and their market selling prices are often higher than those of ordinary edible oils. Due to the prevalence of edible oil adulteration driven by financial interests, the issue of authentication of edible vegetable oils has become a difficult issue highly concerned by consumers and industry. Therefore, it is of great significance to establish an effective method for detecting authentication of edible oil.

The existing national or industrial standards for edible vegetable oils provide various quality indicators that need to be met by edible vegetable oils, and clearly provide that edible vegetable oils should not be blended with other edible oils and non-edible oils, should not be added with flavors or fragrances, and should be marked with processing methods, corresponding quality grades and countries of production of raw materials. The characteristic indicators provided in the standards, such as refractive index, relative density, iodine value, saponification value, and low characteristics of unsaponifiable matters, are greatly affected by variety, and processing and storage time, while for the fatty acid composition, only the relative content range of each fatty acid instead of a characteristic composition is provided, so adulterated edible vegetable oils cannot be effectively distinguished from authentic ones. Thus, it is necessary to establish a rapid, simple and non-destructive authentication technology for edible vegetable oils.

At present, the rapid identification methods for the authenticity of edible vegetable oils include Fourier transform infrared spectroscopy, near infrared spectroscopy, electronic noses, electronic tongues, nuclear magnetic resonance, etc., which are rapid, simple and non-destructive.

However, all of the above methods need to be combined with a chemometric method to establish an edible oil authenticity identification model for determining unknown samples. In the modeling process of the conventional chemometric method, a sufficient amount of edible vegetable oil and edible vegetable oil samples correspondingly blended with cheap oils or fats are required. However, since it is very hard to determine the types and numbers of adulterants in edible oils, more than one kind of cheaper oils were adulterated into expensive edible oil to mask existing adulteration detection methods. The number of combinatorial adulterations of different proportions of several cheap oils can circumvent detection. Considering the cost and operability, the conventional methods often only enable effective identification on one or two known cheap fats added to the edible vegetable oil. Obviously, these technologies have great limitations. Unscrupulous traders can avoid the above technology by simultaneously adding two or more cheap fats or directly adding mixed fats (such as recycled cooking oil). Therefore, a multivariate adulteration detection technology for edible vegetable oils is urgently required to be developed.

SUMMARY OF THE INVENTION

One of the objectives of this invention is to provide a method for detecting multivariate adulteration of an edible oil based on near-infrared spectroscopy, aiming at the defect that it is difficult to quickly and accurately identify whether the edible oil is adulterated in the prior art. In certain aspects, the invention uses the strategy of simplex linear programming theory to select important variables having a greatest contribution to classification of authentic and potential adulterating edible vegetable oils with the help of a variable selection method such as principal component analysis, partial least squares discriminant analysis or partial least squares discriminant analysis, and establishes a one class classification model for a high-priced edible vegetable oil by using a modeling method such as a one class partial least squares method, soft independent modeling of class analogy or a one class support vector machine, thereby realizing multivariate adulteration detection on several types of potential adulterated edible oils, and providing a powerful technical support for ensuring the authenticity of edible vegetable oils.

In one aspect, the invention relates to a method for detecting multivariate adulteration of an edible oil based on a near-infrared spectroscopy. In certain embodiments, the method includes the following steps:

S1: selecting authentic edible oils and potentially adulterating edible oils as samples; and acquiring near-infrared spectra of the samples by using the near-infrared spectrometer;

S2: performing standard normal transformation data preprocessing on the acquired original near-infrared spectra of the samples; subtracting an average value of absorbance of spectral points from the acquired near-infrared spectra, dividing the spectral data by a standard deviation of the spectral data to obtain preprocessed near-infrared spectra as standard spectra, and establishing a near-infrared spectral database of the edible oils;

S3: establishing a classification model between the authentic edible oils and potentially adulterating edible oils by using a chemometric method to select important variables for distinguishing the authentic edible oils from the adulterated edible oils; and establishing a one class classification model of the authentic edible oil by using the determined critical variables, wherein the one class classification model is a multivariate adulteration detection model; and S4: providing an edible oil sample for testing; acquiring near-infrared spectra of the tested edible oil sample by using the near-infrared spectrometer; processing the acquired near-infrared spectra of the tested edible oil sample by using the preprocessing method in step S2 to obtain standard spectral data of the tested edible oil sample; and determining authenticity of the tested edible oil sample by using the multivariate adulteration detection model established in step S3.

In certain embodiments, a formula for preprocessing the near-infrared spectra of the samples in step S2 is:

$$Z_{ij} = \frac{x_{ij} - \bar{x}_i}{S_i}$$

$$\bar{x}_i = \frac{1}{p} \sum_{j=1}^{p} x_{ij}$$

$$S_i = \sqrt{\frac{1}{p-1} \sum_{j=1}^{p} (x_{ij} - \bar{x}_i)^2}$$

where $Z_{ij}$ is a spectral point after each sample is preprocessed; $x_{ij}$ is an original spectral point of each sample; $\bar{x}_i$ is an average value of all the spectral points of each sample spectrum; $S_i$ is a standard deviation of spectral data of the sample; i=1, 2, . . . , n; j=1, 2, . . . , p; n is the number of samples, and p is the number of spectral points.

In certain embodiments, the critical variables in step S3 are characteristic wavelengths.

In certain embodiments, the potentially adulterating edible oils are edible oils cheaper than the authentic edible oils.

In certain embodiments, the near-infrared spectra of each sample are repeatedly measured for 2 to 9 times in step S1.

In certain embodiments, step S1 is performed under acquisition conditions of which the acquisition temperature is 20±5° C., the near-infrared spectrum measurement range is 4,000 to 10,000 cm$^{-1}$, the number of scans is 32 times, the resolution is 3.857 cm$^{-1}$, the light path of a sample pool is 2 to 10 mm, and the measurement method is transmission.

In certain embodiments, the chemometric method used in step S3 comprises: a variable selection method including but not limited to principal component analysis, partial least squares discriminant analysis; and a modeling method including but not limited to one class partial least squares method, soft independent modeling of class analogy or a one class support vector machine.

In certain embodiments, establishing the one class classification model in step S3 comprises the steps of: randomly dividing authentic target edible oil samples into two data sets comprising a training set and a validation set, according to a certain ratio; establishing the one class classification model by using the near-infrared spectral information of authentic edible oils in the training set; and validating the one class classification model by using the near-infrared spectral information of the authentic edible oils as the validation set and the adulterated edible oils.

In certain embodiments, determining the authenticity of the tested edible oils by using the multivariate adulteration detection model comprises the steps of: determining a determination threshold according to the distribution of absolute center deviations of the spectral data of the authentic edible oil samples in the training set in the multivariate adulteration detection model; importing the characteristic near-infrared spectral information of the tested edible oil sample into the multivariate adulteration detection model; calculating an absolute center deviation value by the multivariate adulteration detection model; and comparing the value with the threshold to identify the authenticity of the tested edible oil sample.

In another aspect of the invention, the method for detecting multivariate adulteration of an edible oil includes providing an edible oil sample for testing; acquiring near-infrared spectra of the tested edible oil sample by using a near-infrared spectrometer; processing the acquired near-infrared spectra of the tested edible oil sample to obtain standard spectral data of the tested edible oil sample; and determining authenticity of the tested edible oil sample by using the multivariate adulteration detection model constructed using samples of authentic edible oils and potentially adulterating edible oils.

In certain embodiments, the multivariate adulteration detection model is constructed by the steps of acquiring near-infrared spectra of the samples by using the near-infrared spectrometer; performing standard normal transformation data preprocessing on the acquired original near-infrared spectra of the samples; subtracting an average value of absorbance of spectral points from the acquired near-infrared spectra, dividing the spectral data by a standard deviation of the spectral data to obtain preprocessed near-infrared spectra as standard spectra, and establishing a near-infrared spectral database of the edible oils; and for an authentic edible oil, establishing a classification model between the authentic edible oil and potentially adulterating edible oils by using a chemometric method to determine critical variables for distinguishing the authentic edible oil from the adulterated edible oils; and establishing a one class classification model of the authentic edible oil by using the determined critical variables, wherein the one class classification model is a multivariate adulteration detection model.

In certain embodiments, a formula for preprocessing the near-infrared spectra of the samples is:

$$Z_{ij} = \frac{x_{ij} - \bar{x}_i}{S_i}$$

$$\bar{x}_i = \frac{1}{p} \sum_{j=1}^{p} x_{ij}$$

$$S_i = \sqrt{\frac{1}{p-1} \sum_{j=1}^{p} (x_{ij} - \bar{x}_i)^2}$$

where $Z_{ij}$ is a spectral point after each sample is preprocessed; $x_{ij}$ is an original spectral point of each sample; $\bar{x}_i$ is an average value of all the spectral points of each sample spectrum; $S_i$ is a standard deviation of spectral data of the sample; i=1, 2, . . . , n; j=1, 2, . . . , p; n is the number of samples, and p is the number of spectral points.

In certain embodiments, the critical variables are characteristic wavelengths.

In certain embodiments, establishing the one class classification model comprises the steps of: randomly dividing authentic target edible oil samples into two data sets comprising a training set and a validation set, according to a certain ratio; establishing the one class classification model by using the near-infrared spectral information of an authentic target edible oil in the training set; and validating the one class classification model by using the near-infrared spectral information of the authentic edible oil as the validation set and the adulterated edible oil.

In certain embodiments, determining the authenticity of the tested edible oil sample by using the multivariate adulteration detection model comprises the steps of: determining a determination threshold according to the distribution of absolute center deviations of the spectral data of the authentic edible oil samples in the training set in the multivariate adulteration detection model; importing the characteristic near-infrared spectral information of the tested edible oil sample into the multivariate adulteration detection model; calculating an absolute center deviation value by the multivariate adulteration detection model; and comparing the value with the threshold to identify the authenticity of the tested edible oil sample.

According to the invention the method for identifying multivariate adulteration of an edible oil based on near-infrared spectroscopy is simple to operate and has no special requirements for operators, rapid, is non-destructive, short in sample detection time, environmentally friendly and low in detection cost, does not need any chemical reagent, and can be effectively applied to on-site supervision and detection of the edible oil market, with broad prospects.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present there between. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the phrase "at least one of A, B, and C" should be construed to mean a logical (A or B or C), using a non-exclusive logical OR. As used herein, the term "and/or" includes any and all combinations of one or more of the associated listed items.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

In one aspect of the invention, a method for detecting multivariate adulteration of an edible oil based on near-infrared spectroscopy comprises the following steps:

(1) Model Construction:

S1, near-infrared spectral signal acquisition: selecting multiple varieties of authentic (or high-priced) edible oils and potentially adulterating edible oils as samples, and acquiring near-infrared spectra of the samples through the near-infrared spectrometer;

S2, preprocessing of near-infrared spectra and establishment of a near-infrared spectral database of edible oils: performing standard normal transformation data preprocessing on the acquired original near-infrared spectra of the samples; subtracting an average value of absorbance of spectral points from the original near-infrared spectra, dividing the spectral data by a standard deviation of the spectral data to obtain preprocessed near-infrared spectra as standard spectra, and establishing a near-infrared spectral database of the edible oils;

S3, establishment of a multivariate adulteration detection model for an edible oil: for an authentic (or high-priced) edible oil, establishing a classification model between the high-priced edible oil and cheap edible oils by using chemometrics, and selecting critical variables (critical variables for distinguishing the authentic edible oil from the cheap edible oils) having a greatest classification contribution to establish a one class classification model of the high-priced edible oil, that is, a multivariate adulteration detection model of the authentic edible oil; and (2) Model Application:

providing an edible oil sample for testing, acquiring near-infrared spectra of the tested edible oil sample by using the near-infrared spectrometer, preprocessing the same by the preprocessing method in step S2 to obtain standard spectral data of the tested edible oil sample, and determining the authenticity of the tested edible oil sample by using the multivariate adulteration detection model established in step S3.

A formula for preprocessing the near-infrared spectra in step S2 is:

$$Z_{ij} = \frac{x_{ij} - \bar{x}_i}{S_i}$$

$$\bar{x}_i = \frac{1}{p}\sum_{j=1}^{p} x_{ij}$$

$$S_i = \sqrt{\frac{1}{p-1}\sum_{j=1}^{p}(x_{ij}-\bar{x}_i)^2}$$

where $Z_{ij}$ is a spectral point after each sample is preprocessed; $x_{ij}$ is an original spectral point of each sample; $\bar{x}_i$ is an average value of all the spectral points of each sample spectrum; $S_i$ is a standard deviation of spectral data of the sample; i=1, 2, ..., n; j=1, 2, ..., p; n is the number of samples, and p is the number of spectral points.

The critical variables having a greatest classification contribution, selected in step S3, are characteristic wavelengths.

The near-infrared spectra of each sample are repeatedly measured for 2 to 9 times in step S1.

The spectral acquisition conditions in step S1 are as follows: the acquisition temperature is 20±5° C., the near-infrared spectrum measurement range is 4,000 to 10,000 $cm^{-1}$, the number of scans is 32 times, the resolution is 3.857 $cm^{-1}$, the light path of a sample pool is 2 to 10 mm, and the measurement method is transmission.

The chemometric method used in step S3 comprises: a variable selection method such as principal component analysis, partial least squares discriminant analysis or partial least squares discriminant analysis of orthogonal correction, and a modeling method such as a one class partial least squares method, soft independent modeling of class analogy or a one class support vector machine.

The authentic target edible oil samples are randomly divided into two data sets, namely a training set and a validation set, in a certain ratio (e.g., 8:2 or 6:4). A one class classification model is established by using the near-infrared spectral information of the authentic target edible oil in the training set, and the model is verified by using the near-infrared spectral information of the authentic edible oil (the validation set) and the adulterated edible oil.

A determination threshold is determined according to the distribution of absolute center deviations of the spectral data of the authentic samples in the training set in the model, the characteristic near-infrared spectral information of the sample to be tested is imported into the model, and an absolute center deviation value is calculated by the model and compared with the threshold to identify the authenticity of the sample to be tested.

In another aspect of the invention, the method for detecting multivariate adulteration of an edible oil includes providing an edible oil sample for testing; acquiring near-infrared spectra of the tested edible oil sample by using a near-infrared spectrometer; processing the acquired near-infrared spectra of the tested edible oil sample to obtain standard spectral data of the tested edible oil sample; and determining authenticity of the tested edible oil sample by using the multivariate adulteration detection model constructed using samples of authentic edible oils and potentially adulterating edible oils as disclosed above.

These and other aspects of the present invention are further described in the following section. Without intending to limit the scope of the invention, further exemplary implementations of the present invention according to the embodiments of the present invention are given below, where the percent is mass percent.

A. Near-infrared spectral signal acquisition of samples: 33 pure linseed oil samples (20 training set samples and 13 validation set samples divided by a K-S algorithm in a ratio of 6:4; respective 6 cottonseed oil, soybean oil, rapeseed oil, corn oil and sunflower oil samples, and 3 adulterated oil samples; adding respective 3 cottonseed oil, soybean oil, rapeseed oil, corn oil and sunflower oil samples into the linseed oil samples in a ratio of 5% to obtain 15 samples. In addition, the soybean oil, the rapeseed oil and the corn oil are added into the linseed oil in four different ratios of 1:1:0, 1:0:1, 0:1:1, 1:1:1 by an amount of 5% to obtain 36 samples. The near-infrared spectra of the above 114 samples are acquired under the following conditions: the acquisition temperature is 16±2° C., the near-infrared spectrum measurement range is 4,000 to 10,000 cm$^{-1}$, the number of scans is 32 times, the resolution is 3.857 cm$^{-1}$, the light path of a sample pool is 2 mm, and the measurement method is transmission.

B. Preprocessing of near-infrared spectra of samples: it is found through experimental studies and literature reports that different preprocessing on the spectra before modeling has quite different influence on the modeling. The method uses standard normal transformation data preprocessing to obtain preprocessed spectra of linseed oil and adulterated linseed oil samples and other edible vegetable oil samples for adulteration. A near-infrared spectral database of the above 33 pure linseed oil samples and respective 6 cottonseed oil, soybean oil, rapeseed oil, corn oil and sunflower oil samples is established.

Figure 1:
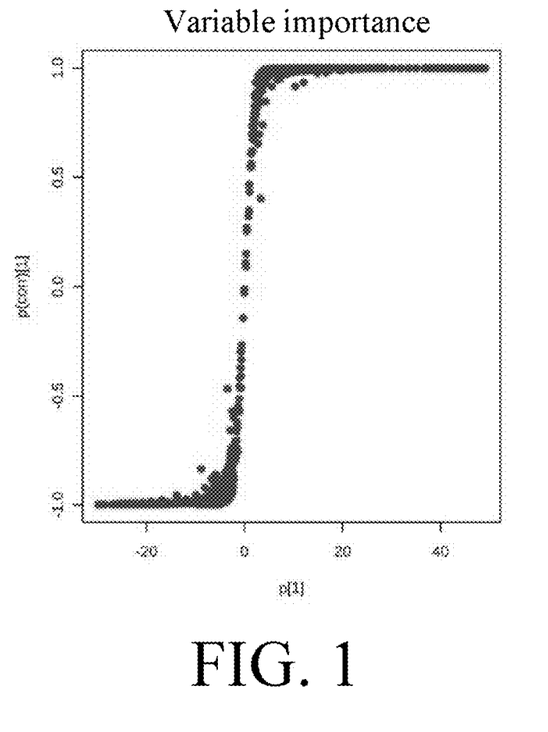
FIG. 1 is a diagram of variable importance according to an embodiment of the present invention.
Figure 2:
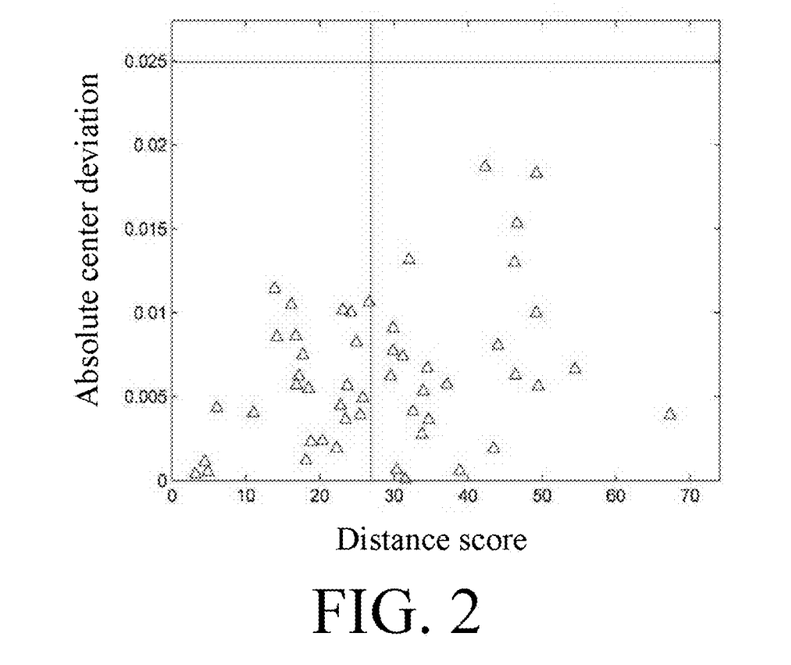
FIG. 2 is a diagram of a model misjudgment rate before variable selection according to an embodiment of the present invention.
Figure 3:
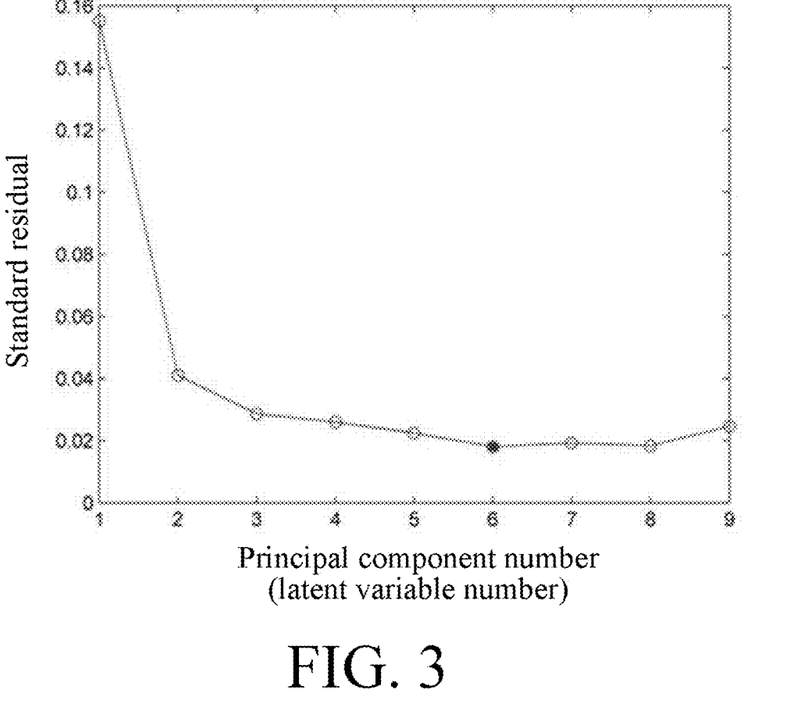
FIG. 3 is a diagram of the number of latent variables according to an embodiment of the present invention.
Figure 4:
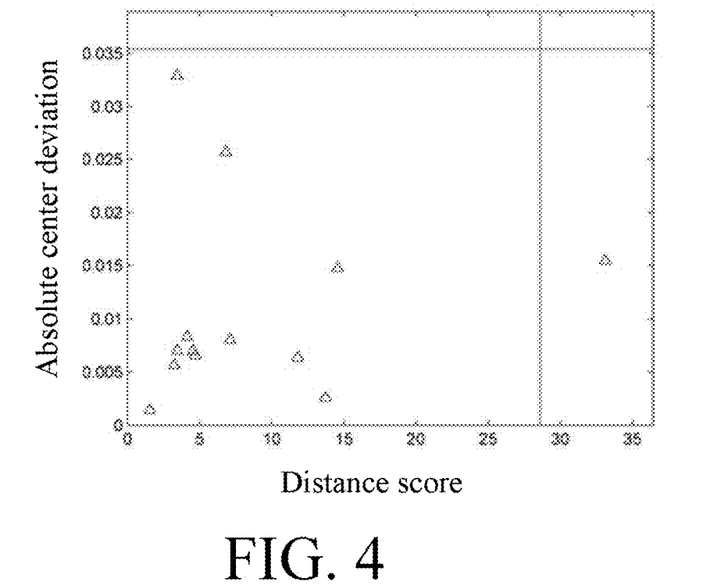
FIG. 4 is a judgment diagram of pure linseed oil according to an embodiment of the present invention.
Figure 5:
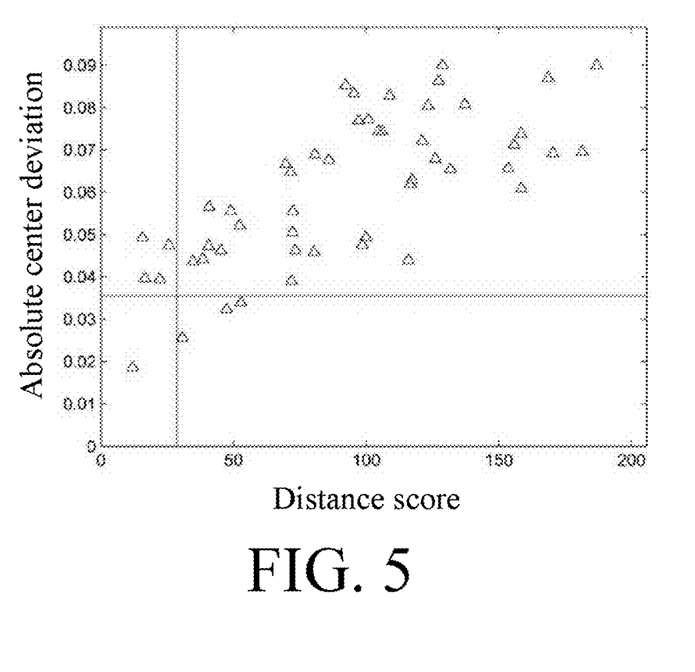
FIG. 5 is a judgment diagram of adulterated linseed oil according to an embodiment of the present invention.

C. Establishment and validation of a linseed oil authenticity identification model: performing standard normal transformation data preprocessing on 114 pieces of sample information in a Matlab® R2014a, performing Pareto scale preprocessing on the preprocessed spectra of the 20 linseed oil samples in the training set and the 30 samples of cottonseed oil, soybean oil, rapeseed oil, corn oil and sunflower oil by using a MetaboAnalyst2.0 data processing platform, and performing variable selection on the spectral information in combination with orthogonal least squares-discriminant analysis, as shown in FIG. 1, wherein the X axis represents a fitting covariance vector Cov(t,X), the Y axis represents a correlation coefficient vector Corr(t,X), and the calculation formulas of the two are as follows:

$$Cov(t,X_i)=t^T X_i/(N-1)$$

$$Corr(t,Xi)=Cov(t,X_i)/s_t s_{Xi}$$

where i=1, 2, . . . , n; n is the number of variables, N is the number of samples, t is a score vector in a prediction component of orthogonal partial least squares discriminant analysis, $s_t$ is a standard deviation of the model prediction score vector, and $s_x$ is an estimated standard deviation vector of each variable. Thus, 184 critical variables (i.e. characteristic wavelengths) at the upper right and lower left corners of FIG. 1 are selected, as shown in Table 1. As shown in FIG. 2, the model established using the full spectra of near-infrared spectra has a high misjudgment rate, all the adulterated linseed oil is identified as authentic linseed oil, and FIG. 5 shows identification on the adulterated linseed oil after variable selection. In the four quadrants, the lower two quadrants are judged to be linseed oil, and the upper two quadrants are judged to be adulterated linseed oil. A linseed oil authenticity identification model is established based on 20 linseed oil samples in the training set, 13 linseed oil samples in the validation set and 51 adulterated linseed oil samples after the variable selection in combination with a one class partial least squares method, and is validated. As shown in FIG. 3, when the principal component number is 6, the cross validation prediction standard residual of the model is smallest, and the model prediction effect is optimal; as shown in FIG. 4, the judged accuracy of the pure linseed oil is 100%; and as shown in FIG. 5, the judged accuracy of the adulterated linseed oil is 92.16% (47/51).

TABLE 1

Characteristic wavelength table

| Variable selection method | Wavelengths of critical variables (cm$^{-1}$) | Number of critical variables |
|---|---|---|
| Orthogonal partial least squares-discriminant analysis | 3999.64, 4003.497, 4007.354, 4011.211, 4015.068, 4018.925, 4022.781, 4026.638, 4030.495, 4034.352, 4038.209, 4042.066, 4045.923, 4049.78, 4053.637, 4057.494, 4061.351, 4065.208, 4069.065, 4072.922, | 184 |

TABLE 1-continued

Characteristic wavelength table

| Variable selection method | Wavelengths of critical variables (cm$^{-1}$) | Number of critical variables |
|---|---|---|
| | 4076.779, 4080.635, 4084.492, 4088.349, 4092.206, 4096.063, 4099.92, 4103.777, 4107.634, 4111.491, 4115.348, 4119.205, 4123.062, 4126.918, 4130.775, 4134.632, 4138.489, 4142.346, 4146.203, 4150.06, 4153.917, 4157.774, 4161.631, 4165.488, 4169.345, 4173.202, 4177.059, 4180.916, 4184.772, 4188.629, 4192.486, 4238.77, 4242.626, 4246.483, 4250.34, 4254.197, 4258.054, 4261.911, 4265.768, 4269.625, 4273.482, 4277.339, 4281.196, 4285.053, 4288.91, 4292.767, 4296.624, 4300.48, 4304.337, 4308.194, 4312.051, 4315.908, 4319.765, 4323.622, 4327.479, 4331.336, 4335.193, 4339.05, 4342.907, 4346.764, 4350.621, 4354.478, 4400.761, 4404.618, 4408.475, 4412.332, 4416.188, 4420.045, 4423.902, 4427.759, 4431.616, 4435.473, 4439.33, 4443.187, 4447.044, 4450.901, 4454.758, 4458.615, 4462.472, 4466.329, 4470.186, 4474.042, 4477.899, 4481.756, 4485.613, 4489.47, 4493.327, 4497.184, 4501.041, 4504.898, 4508.755, 4512.612, 4516.469, 4520.326, 4524.183, 4528.04, 4531.896, 4535.753, 4651.461, 4655.318, 4659.175, 4663.032, 4666.889, 4670.746, 5634.979, 5638.836, 5642.693, 5646.55, 5650.407, 5654.264, 5658.121, 5661.978, 5665.835, 5669.692, 5673.549, 5677.406, 5681.263, 5685.12, 5688.977, 5692.833, 5696.69, 5700.547, 5704.404, 5708.261, 5781.543, 5785.4, 5789.257, 5793.114, 5796.971, 5800.828, 5804.685, 5808.542, 5812.398, 5816.255, 5820.112, 5823.969, 5827.826, 5831.683, 5835.54, 5839.397, 5843.254, 5847.111, 5850.968, 5854.825, 5858.682, 5862.539, 5904.965, 5908.822, 5912.679, 5916.536, 5920.393, 5924.25, 5928.106, 5931.963, 5935.82, 5939.677, 5943.534, 5947.391, 5951.248, 5955.105, 5958.962, 5962.819, 5966.676, 5970.533 | |

The foregoing description of the exemplary embodiments of the invention has been presented only for the purposes of illustration and description and is not intended to be exhaustive or to limit the invention to the precise forms disclosed. Many modifications and variations are possible in light of the above teaching.

While there has been shown several and alternate embodiments of the present invention, it is to be understood that certain changes can be made as would be known to one skilled in the art without departing from the underlying scope of the invention as is discussed and set forth above and below including claims and drawings. Furthermore, the embodiments described above are only intended to illustrate the principles of the present invention and are not intended to limit the scope of the invention to the disclosed elements.

What is claimed is:

1. A method for detecting multivariate adulteration of an edible oil based on a near-infrared spectrometer, comprising the steps of:

S1: selecting authentic edible oils and potentially adulterating edible oils as samples; and acquiring near-infrared spectra of the samples by using the near-infrared spectrometer;

S2: performing standard normal transformation data preprocessing on the acquired original near-infrared spectra of the samples; subtracting an average value of absorbance of spectral points from the acquired near-infrared spectra, dividing the spectral data by a standard deviation of the spectral data to obtain preprocessed near-infrared spectra as standard spectra, and establishing a near-infrared spectral database of the edible oils;

S3: establishing a classification model between the authentic edible oils and potentially adulterating edible oils by using a chemometric method to determine critical variables for distinguishing the authentic edible oils from the adulterated edible oils; and establishing a one class classification model of the authentic edible oil by using the determined critical variables, wherein the one class classification model is a multivariate adulteration detection model; and S4: providing an edible oil sample for testing; acquiring near-infrared spectra of the tested edible oil sample by using the near-infrared spectrometer; processing the acquired near-infrared spectra of the tested edible oil sample by using the preprocessing method in step S2 to obtain standard spectral data of the tested edible oil sample; and determining authenticity of the tested edible oil sample by using the multivariate adulteration detection model established in step S3.

2. The method according to claim 1, wherein a formula for preprocessing the near-infrared spectra of the samples in step S2 is:

$$Z_{ij} = \frac{x_{ij} - \bar{x}_i}{S_i}$$

$$\bar{x}_i = \frac{1}{p}\sum_{j=1}^{p} x_{ij}$$

$$S_i = \sqrt{\frac{1}{p-1} \sum_{j=1}^{p} (x_{ij} - \bar{x}_i)^2}$$

where $Z_{ij}$ is a spectral point after each sample is preprocessed; $x_{ij}$ is an original spectral point of each sample; $\bar{x}_i$ is an average value of all the spectral points of each sample spectrum; $S_i$ is a standard deviation of spectral data of the sample; i=1, 2, . . . , n; j=1, 2, . . . ,p; n is the number of samples, and p is the number of spectral points.

3. The method according to claim 1, wherein the critical variables in step S3 are characteristic wavelengths.

4. The method according to claim 1, wherein the near-infrared spectra of each sample are repeatedly measured for 2 to 9 times in step S1.

5. The method according to claim 1, wherein step S1 is performed under acquisition conditions of which the acquisition temperature is 20±5° C., the near-infrared spectrum measurement range is 4,000 to 10,000 cm$^{-1}$, the number of scans is 32 times, the resolution is 3.857 cm$^{-1}$, the light path of a sample pool is 2 to 10 mm, and the measurement method is transmission.

6. The method according to claim 1, wherein the chemometric method used in step S3 comprises:
 a variable selection method comprising principal component analysis, partial least squares discriminant analysis or partial least squares discriminant analysis of orthogonal correction; and
 a modeling method comprising a one class partial least squares method, soft independent modeling of class analogy or a one class support vector machine.

7. The method according to claim 1, wherein establishing the one class classification model in step S3 comprises the steps of:
 randomly dividing authentic edible oil samples into two data sets comprising a training set and a validation set, according to a certain ratio;
 establishing the one class classification model by using the near-infrared spectral information of an authentic target edible oil in the training set; and
 validating the one class classification model by using the near-infrared spectral information of the authentic edible oil as the validation set and the adulterated edible oil.

8. The method according to claim 7, wherein determining the authenticity of the tested edible oil sample by using the multivariate adulteration detection model comprises the steps:
 determining a determination threshold according to the distribution of absolute center deviations of the spectral data of the authentic edible oil samples in the training set in the multivariate adulteration detection model;
 importing the characteristic near-infrared spectral information of the tested edible oil sample into the multivariate adulteration detection model;
 calculating an absolute center deviation value by the multivariate adulteration detection model; and
 comparing the value with the threshold to identify the authenticity of the tested edible oil sample.

9. A method for detecting multivariate adulteration of an edible oil, comprising the steps of:
 providing an edible oil sample for testing;
 acquiring near-infrared spectra of the tested edible oil sample by using a near-infrared spectrometer;
 processing the acquired near-infrared spectra of the tested edible oil sample to obtain standard spectral data of the tested edible oil sample; and
 determining authenticity of the tested edible oil sample by using a multivariate adulteration detection model constructed using samples of authentic edible oils and potentially adulterating edible oils,
 wherein the multivariate adulteration detection model is constructed by the steps of:
 acquiring near-infrared spectra of the samples by using the near-infrared spectrometer;
 performing standard normal transformation data preprocessing on the acquired original near-infrared spectra of the samples; subtracting an average value of absorbance of spectral points from the acquired near-infrared spectra, dividing the spectral data by a standard deviation of the spectral data to obtain preprocessed near-infrared spectra as standard spectra, and establishing a near-infrared spectral database of the edible oils; and
 for an authentic edible oil, establishing a classification model between the authentic edible oil and potentially adulterating edible oils by using a chemometric method to determine critical variables for distinguishing the authentic edible oil from the adulterated edible oils; and establishing a one class classification model of the authentic edible oil by using the determined critical variables, wherein the one class classification model is a multivariate adulteration detection model.

10. The method according to claim 9, wherein a formula for preprocessing the near-infrared spectra of the samples is:

$$Z_{ij} = \frac{x_{ij} - \bar{x}_i}{S_i}$$

$$\bar{x}_i = \frac{1}{p} \sum_{j=1}^{p} x_{ij}$$

$$S_i = \sqrt{\frac{1}{p-1} \sum_{j=1}^{p} (x_{ij} - \bar{x}_i)^2}$$

where $Z_{ij}$ is a spectral point after each sample is preprocessed; $x_{ij}$ is an original spectral point of each sample; $\bar{x}_i$ is an average value of all the spectral points of each sample spectrum; S1 is a standard deviation of spectral data of the sample; i=1, 2, . . . , n; j=1, 2, . . . , p; n is the number of samples, and p is the number of spectral points.

11. The method according to claim 9, wherein the critical variables are characteristic wavelengths.

12. The method according to claim 9, wherein establishing the one class classification model comprises the steps of:
 randomly dividing authentic target edible oil samples into two data sets comprising a training set and a validation set, according to a certain ratio;
 establishing the one class classification model by using the near-infrared spectral information of an authentic target edible oil in the training set; and
 validating the one class classification model by using the near-infrared spectral information of the authentic edible oil as the validation set and the adulterated edible oil.

13. The method according to claim 12, wherein determining the authenticity of the tested edible oil sample by using the multivariate adulteration detection model comprises the steps:

determining a determination threshold according to the distribution of absolute center deviations of the spectral data of the authentic edible oil samples in the training set in the multivariate adulteration detection model;

importing the characteristic near-infrared spectral information of the tested edible oil sample into the multivariate adulteration detection model;

calculating an absolute center deviation value by the multivariate adulteration detection model; and comparing the value with the threshold to identify the authenticity of the tested edible oil sample.

* * * * *